United States Patent [19]

Bush et al.

[11] Patent Number: 5,089,045
[45] Date of Patent: Feb. 18, 1992

[54] SUBSTITUTED 3,6,7,8-TETRAHYDROIMIDAZO[4,5-D][1,3]DIAZEPINE-8-OL HERBICIDES

[75] Inventors: Brian D. Bush, Cherry Hinton; Duncan A. Gates, Saffron Walden; David Langley, London, all of England

[73] Assignee: Schering Agrochemicals Limited, England

[21] Appl. No.: 522,517

[22] Filed: May 11, 1990

[30] Foreign Application Priority Data

May 13, 1989 [GB] United Kingdom ............... 8911029

[51] Int. Cl.$^5$ ............... C07D 487/04; A01N 43/64; A01N 43/48
[52] U.S. Cl. ............... 71/92; 435/252.1; 536/17.3; 536/17.4; 536/27; 536/28; 540/568
[58] Field of Search ............... 540/568; 71/92

[56] References Cited

PUBLICATIONS

Omura et al., (I), Chemical Abstract vol. 105:153462p, 1986.

Omura et al., (II), Chemical Abstract vol. 107:76096j, 1987.

Primary Examiner—Mukund J. Shah
Assistant Examiner—Philip I. Datlow
Attorney, Agent, or Firm—Ostrolenk, Faber, Gerb & Soffen

[57] ABSTRACT

Herbicidal 3,6,7,8-tetrahydroimidazo[4,5-d]-[1,3]diazepin-8-ol derivatives of the formula:

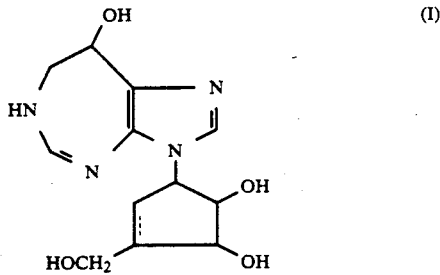

and sugar conjugates thereof, compositions containing them, and a process for their preparation.

6 Claims, No Drawings

SUBSTITUTED 3,6,7,8-TETRAHYDROIMIDAZO[4,5-D][1,3]DIAZEPINE-8-OL HERBICIDES

This invention concerns herbicidal compounds, some of which are new, a process for their preparation, and compositions containing them.

We have found that the 3,6,7,8-tetrahydroimidazo-[4,5-d]-[1,3]diazepin-8-ol derivatives of the formula:

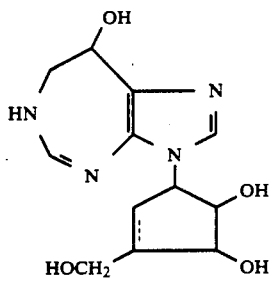

and sugar conjugates thereof, are herbicidally active.

As is conventional, the dotted line in the formula indicates that the bond between the two carbon atoms may be either a single bond or a double bond. Those compounds where there is a single bond between the relevant carbon atoms are novel, and in one aspect this invention provides them per se.

The sugar conjugates of the compounds of formula I as that term is used herein are those where one or more of the —OH groups or the —NH group in the molecule is replaced with a group —OR or —NR respectively, where R is a sugar moiety, especially a hexose moiety, and particularly a glucose moiety. It is preferred that just a single sugar group is present in the sugar conjugates. It is also preferred that this is where the group -OR replaces the —OH in the —CH$_2$OH group in formula I.

The term 'compounds of formula I' is used hereinafter to include sugar conjugates.

The compounds of formula I are herbicidally active against a range of broad-leaved and grassy weeds. They may thus be of use as herbicides, either as total herbicides, or possibly as selective herbicides, particularly in the control of a range of weeds in cereals or other crops, eg wheat, rice, barley, maize, soya beans, oilseed rape, cotton or sugar beet.

In another aspect, the invention provides the use of one or more compounds of formula I as a herbicide, and also a herbicidal composition which comprises one or more compounds of formula I in association with a suitable carrier and/or surface active agent.

The compounds of formula I each have a number of optical centres and thus a number of optical isomers. This invention is not limited in any way to specific optical isomers, but as is usual in such compounds, some optical isomers may well exhibit greater activity in certain respects than others.

Preferred compounds of the invention include 3-[2,3-dihydroxy-4-(hydroxymethyl)cyclopentyl]-3,6,7,8-tetrahydroimidazo[4,5-d][1,3]diazepin-8-ol (hereinafter referred to as 'Compound A'), 3-[2,3-dihydroxy-4-(β-D-glucosyloxymethyl)cyclopentyl]-3,6,7,8-tetrahydroimidazo[4,5-d][1,3]diazepin-8-ol (ie a glucose conjugate of Compound A), and 3-[4,5-dihydroxy-3-(hydroxymethyl)cyclopent-2-en-1-yl]-3,6,7,8-tetrahydroimidazo[4,5-d][1,3]-diazepin-8-ol (hereinafter referred to as 'Compound B'). The preferred optical isomers of these compounds are believed to be 8R-3-(1R,2S,3R,4R)-2,3-dihydroxy-4-(hydroxymethyl)cyclopentyl]-3,6,7,8-tetrahydroimidazo[4,5-d][1,3]diazepin-8-ol (hereinafter referred to as 'Compound A1'), the corresponding 4-(β-D-glucosyloxymethyl) derivative thereof (hereinafter referred to as 'Compound A2'), 8R-3-[(1R,2S,3R,4S)-2,3-dihydroxy-4-(hydroxymethyl)-cyclopentyl]-3,6,7,8-tetrahydroimidazo[4,5-d][1,3]diazepin-8-ol (hereinafter referred to as 'Compound A3'), and 8R-3-[(1R,4R,5S)-4,5-dihydroxy-3-(hydroxymethyl)cyclopent-2-en-1-yl]-3,6,7,8-tetrahydroimidazo[4,5-d][1,3]-diazepin-8-ol (hereinafter referred to as 'Compound B1').

The compositions usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredients comprise from 0.01 to 5% by weight of the formulation applied.

The carrier may be water, in which case an organic solvent may also be present, though this is not usually employed.

The carrier may alternatively be a water immiscible organic solvent in which the compounds are dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent eg 2-methoxyethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the present compounds with a propellant, eg a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, eg the sulphonated condensation product of oleic acid and N-methyl taurine or the dialkyl sulphosuccinates eg the sodium sulphonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers eg sorbitan fatty acid esters, condensation products of such esters with ethylene oxide eg polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds may be admixed with inorganic compounds, eg $(NH_4)_2SO_4$, an oil, or another pesticide, eg a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially glyphosate, metsulfuron methyl, sulfometuron, isoproturon, methabenzthiazuron, trifluralin, ioxynil, bromoxynil, benazolin, mecoprop, fluroxypyr, alachlor, acifluorfen, lactofen, metribuzin, pendimethalin, ethofumesate, benfuresate, and phenmedipham.

The present compounds may be applied to plants, the soil, land or aquatic areas, and particularly to a locus at which a crop is growing. The compounds are particularly active post-emergence. They may be applied at rates of from 0.02 to 2 kg/ha, especially from 0.1 to 1 kg/ha.

The compounds of the invention may be prepared by the processes discussed below.

Thus according to a further aspect of the invention we provide a process for the production of a compound of formula I which comprises the step of cultivating a microorganism capable of producing the compound of formula I, and if desired isolating said compound therefrom.

Microorganisms capable of producing the compounds of the invention may readily be identified by using a small scale test and analysing a test sample obtained from fermentation of the microorganism by high performance liquid chromatography.

In particular the microorganism to be used in the process according to the invention is a previously undescribed strain of microorganism deposited on 13th April 1989 in the permanent culture collection of the National Collection of Industrial and Marine Bacteria, Torry Research Station, 135 Abbey Road, Aberdeen, Scotland under accession no. NCIMB 40131. NCIMB 40131 is an actinomycete characterized as Amycolatopsis spp (Lechevier et al Int J Syst. Bacteriol 36, 29-37 (1986)) on the basis of the following taxonomic markers:
wall chemotype IV, containing meso-diaminopimelic acid, arabinose and galactose as diagnostic sugars (whole cell sugar pattern A);
no mycolic acids present
phospholipid pattern II, thus containing phosopatidyl ethanolamine as diagnostic lipid.

The generic status of the organisms was also confirmed using actinophage specific for Amycolatopsis species (Prauser W2, W4, W7, W11).

The characteristics of NCIMB 40131 are given in Example 6 below.

The invention provides in a further aspect the microorganism NCIMB 40131 per se and mutants thereof.

Mutants of the above strain may arise spontaneously or may be produced by a variety of methods including those outlined in Techniques for the Development of Microorganisms by H I Adler in "Radiation and Radioisotopes for Industrial Microorganisms", Proceedings of the Symposium, Vienna 1973, p241, International Atomic Energy Authority. Such methods include ionising radiation, chemical methods eg treatment with N-methyl-N'-nitro-N-nitrosoguanidine (NTG), heat, genetic techniques, such as recombination, transduction, transformation, lysogenisation and lysogenic conversion, and selective techniques for spontaneous mutants.

According to a still further aspect of the invention, we provide the genetic material of NCIMB 40131 and mutants thereof that participates in the synthesis of the compounds of formula I. Such material may be obtained using conventional genetic engineering techniques including those outlined by D A Hopwood in "Cloning Genes for Antibiotic Biosynthesis in Streptomyces Spp : Production of a Hybrid Antibiotic" p 409–413 in Microbiology 1985, Ed L Lieve, American Society of Microbiology, Washington DC 1985. Such techniques may be used in a similar manner to that described previously for cloning antibiotic biosynthetic genes, including the biosynthetic genes for actinorhodin (Malpartida, F and Hopwood, D A 1984, Nature 309, p 462–464), erythromycin (Stanzak, R et al, 1986, Biotechnology, 4, p 229–232) and an important enzyme involved in penicillin and cephalosporin production in *Acremonium chrysogenum* (Sansom, S M et al, 1985) Nature, 318, p 191–194). The genetic material so obtained may be used, for example, for strain improvement, for production of biosynthetic enzymes for in vitro applications, or for generating novel herbicides by introduction of such material into organisms other than NCIMB 40131.

The production of the compounds of the invention by fermentation of a suitable organism may be effected by conventional means, ie by culturing the organism in the presence of assimilable sources of carbon, nitrogen and mineral salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates.

Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, borate, phosphate, sulphate, chloride and carbonate ions.

Cultivation of the organism will generally be effected at a temperature of from 20° to 40° C. preferably from 25° to 35° C., especially around 28° C., and will desirably take place with aeration and agitation eg by shaking or stirring. The medium may initially be inoculated with a small quantity of a suspension of the sporulated microorganism but in order to avoid a growth lag a vegetative inoculum of the organism may be prepared by inoculating a small quantity of the culture medium with the spore form of the organism, and the vegetative inoculum obtained may be transferred to the fermentation medium, or more preferably to one or more seed stages where further growth takes place before transfer to the principal fermentation medium. The fermentation will generally be carried out in the pH range of 5.5 to 8.5, preferably 5.5 to 7.5. It may be necessary to add a base or an acid to the fermentation medium to keep the pH within the desired range. Suitable bases which may be added include alkali metal hydroxides such as aqueous sodium hydroxide. Suitable acids include mineral acids such as hydrochloric or sulphuric acid.

The fermentation may be carried out for a period of 2-10 days, eg about 5 days. An antifoam may be present to control excessive foaming and added at intervals as required.

The compounds according to the invention are predominantly contained in the fermentation broth. The mycelia may conveniently be removed from the broth by filtration or centrifugation.

For use as agricultural herbicides it may not be necessary to separate the compounds from the fermentation medium in which they are produced.

Where it is desired to separate the compounds of the invention from the whole fermentation this may be carried out by conventional isolation and separation techniques. The isolation techniques may also be applied to the fermentation broth either before or after clarification. It will be appreciated that the choice of isolation techniques may be varied widely.

The compounds of the invention may be isolated and separated by a variety of fractionation techniques, for example adsorption-elution, precipitation, fractional crystallisation, solvent extraction and liquid-liquid partition which may be combined in various ways.

Chromatography on a suitable support in the form of a bed or, more preferably, packed into a column, has been found to be particularly suitable for isolating and separating the compounds of the invention.

Purification and/or separation of the compounds of the invention from the fermentation broth may be conveniently effected by chromatography (including high performance liquid chromatography) on a suitable support such as silica; a non-functional macroreticular adsorption resin for example cross-linked styrene divinyl benzene polymer resins such as Amberlite XAD-2, XAD-4, XAD-16 or XAD-1180 resins (Rohm & Haas Ltd) or Kastell S112 (Montedison); a substituted styrene-divinyl benzene polymer, for example a halogenated (eg brominated) styrene divinyl benzene polymer such as Diaion SP207 (Mitsubishi); an organic solvent-compatible cross-linked dextran such as Sephadex LH20 (Pharmacia UK Ltd), or on reverse phase supports such as hydrocarbon linked silica eg $C_{18}$-linked silica.

Suitable solvents/eluents for the chromatographic purification/separation of the compounds of the invention will, of course, depend on the nature of the column support. When using column supports such as Amberlite XAD-2 and $C_{18}$-linked silica we have found alcohols such as methanol to be particularly suitable, especially when combined with a polar solvent such as water.

The presence of the compounds of the invention during the extraction/isolation procedures may be monitored by conventional techniques such as high performance liquid chromatography or UV spectroscopy or by utilizing the properties of the compounds described hereinafter.

Where a compound of the invention is obtained in the form of a solution in an organic solvent, for example after purification by chromatography, the solvent may be removed by conventional procedures, eg by evaporation, to yield the compound in a solid or crystalline form. If desired, the compounds of the invention may be further purified by the aforementioned chromatographic techniques and/or recrystallisation.

By a suitable combination of the foregoing procedures the compounds of the invention have been isolated as solids. It will be appreciated that the order in which the above purification steps are carried out and the choice of those which are used may be varied widely.

The invention is illustrated by the following Examples.

EXAMPLE 1

Spores of actinomycete NCIMB 40131 were inoculated onto agar slants made up of the following ingredients.

|  | g/l |
| --- | --- |
| Yeast extract (Oxoid L21) | 0.5 |
| Malt extract (Oxoid L39) | 30.0 |
| Mycological peptone (Oxoid L40) | 5.0 |
| Agar No 3 (Oxoid L13) | 15.0 |
| Distilled water to 1 liter | |
| pH approximately 5.4 | |
| and were incubated at 28° C. for 10 days. | |

The mature slant was then covered with 6 ml of a 10% glycerol solution and scraped with a sterile tool to loosen the spores and mycelium 0.4 ml aliquots of the resulting spore suspension were transferred to sterile polypropylene straws which were then heat-sealed and stored in liquid nitrogen vapor until required.

The contents of a single straw were used to inoculate two 50 ml aliquots of a seed medium (A) as follows:

|  | g/l |
| --- | --- |
| D-Glucose | 15.0 |
| Glycerol | 15.0 |
| Soya peptone | 15.0 |
| NaCl | 3.0 |
| $CaCO_3$ | 1.0 |
| Distilled water to 1 liter | |

The unadjusted pH of the medium was 6.7 which was adjusted to pH 7.0 with aqueous sodium hydroxide before autoclaving. The pH of the medium after autoclaving was 7.3.

The two 50 ml volumes of inoculated seed medium were incubated in 250 ml Erlenmeyer flasks at 28° C. for 3 days on a shaker rotating at 250 rpm with a 50 mm diameter orbital motion.

The incubated medium was pooled and used to inoculate at a level of 3%, 20×250 ml Erlenmeyer flasks containing 50 ml of medium (B) of the following composition:

|  | g/l |
|---|---|
| D-Glucose | 2.5 |
| Maltodextrin MD3OE (Roquette (UK) Ltd) | 25.0 |
| Arkasoy 50 (British Arkady Co Ltd) | 12.5 |
| Beet Molasses | 1.5 |
| $KH_2PO_4$ | 0.125 |
| Calcium carbonate | 1.25 |
| MOPS (3-(N-morpholino)propane sulphonic acid) | 21.0 |
| Distilled water to 1 liter |  |
| pH adjusted to 6.5 with 5N NaOH |  |

The flasks were grown, with shaking, at 28° C. for 5 days.

The cells and culture fluid were separated by centrifugation.

EXAMPLE 2

50 ml of seed medium (A) were placed in each of eight 250 ml Erlenmeyer flasks, and the pH was adjusted from an initial value of 6.7 to 7.0 with aqueous sodium hydroxide. After autoclaving, the pH was 7.3. The flasks were each inoculated with 0.2 ml of the spore suspension taken from straws and prepared according to the method described in Example 1 above.

The flasks were incubated at 28° C. for 3 days on a shaker rotating at 250 rpm with a 50 mm diameter orbital motion.

The contents of the eight flasks were pooled and used to inoculate a 20-liter fermenter vessel containing 12 liters of medium (B), the pH being adjusted to 6.5 with 5N NaOH before autoclaving.

The inoculated medium was agitated with conventional impellers rotating at 800 rpm. Aeration of the culture was achieved by dispensing sterile air through the medium at a rate of 0.5 volume of air per volume of culture medium per minute.

Temperature was controlled at 28° C. and excessive foaming overcome by the addition of silicone antifoam. The culture was harvested after 5 days growth and processed as described in Example 1.

100 g of Amberlite XAD-2 resin (Rohm and Haas Limited) was added to 2 liters of aqueous supernatant from the above fermentation, and the mixture was stirred for 20 hours at room temperature. The resin was filtered off and then washed with 250ml portions of 10% aqueous methanol, fractions of approximately 250ml being collected. 5μl Aliquots of each fraction were applied to the growing tips of a number of *Polygonum lapathifolium* plants, which were then grown on in a controlled environment room for 7 days, after which time the plants were assessed for herbicidal effect. Fractions exhibiting herbicidal activity were combined and loaded onto a column of C-18-linked silica (5cm×2cm) packed in water. The column was then washed with 98:2 water:methanol, fractions of approximately 250ml being collected. Fractions exhibiting herbicidal activity in a repetition of the above test were combined, evaporated and subjected to preparative hplc on Dynamax C-18 (250mm×21mm, Rainin Instruments) using a gradient system of water and methanol. Material eluting from the column was monitored by UV spectroscopy at 280nm. The biologically-active fractions were analysed by hplc on Dynamax C-18 (250mm×4.6mm, Rainin Instruments) using water as the eluting phase at a flow rate of 1ml/min, and those fractions containing similar components (retention times of compounds B1, A3, A1 and A2 being approximately 10 minutes, 17 minutes, 21 minutes and 23 minutes respectively) were combined, evaporated and subjected to further preparative hplc on a Zorbax TMS (250mm×10mm) column, monitoring the column eluant at 280nm. Evaporation of the biologically-active fractions yielded compounds A and B and the glucose conjugates of each (where the glucose moiety replaces the hydrogen atom of the —OH group in the group —$CH_2OH$) as solids.

Their structures were confirmed by UV, nmr and mass spectroscopy, the characteristic peaks of the main compounds being as follows:

Compound B1 (Retention Time Approx 10 Mins)

UV (methanol): 279nm

Mass Spectrum (Thermospray): 281 ($M+H^+$)

NMR (300MHz, $D_2O$): δ7.25 (1H,s), 7.05 (1H,s), 5.80 (1 H,d), 5.22 (1H,d), 5.05 (1H,d), 4.55 (1 H,d), 4.20 (2H,s), 4.10 (1H,m), 3.35 (1 H,d), 3.20 (1 H,d).

Compound A1 (Retention Time Approx 21 Mins)

UV (methanol): 282nm

Mass Spectrum (Thermospray): 283 ($M+H^+$)

NMR (300MHz, $D_2O$) δ7.50 (1H,s), 7.05 (1H,s), 5.02 (1H,d), 4.50 (1H,m), 4.20 (1H,dd), 3.90 (1H,dd), 3.55 (2H,d), 3.40 (1H,dd), 3.30 (1H,d), 2.30 (1H,m), 2.10 (1H,m), 1.48 (1H,m)

Compound A2 (Retention Time Approx 23 Mins)

UV (methanol): 281nm

Mass Spectrum (Fast atom bombardment, thioglycerol):

467 ($M+Na^+$)

445 ($M+H^+$)

NMR (300MHz, $D_2O$): δ7.40 (1H,s), 7.05 (1H,s), 5.05 (1H,d), 4.55 (1H,m), 4.41 (1H,d), 4.20 (1H,dd), 4.05 (1H,m), 3.75 (1H,d), 3.60 (1H,dd), 3.50 (2H,m), 3.2-3.4 (6H,m), 2.30 (2H,m), 1.45 (1H,m).

Compound A3 (Retention Time Approx 17 Mins)

UV (methanol): 280nm

Mass Spectrum (Thermospray): 283 (M+H ) NMR (300MHz, $D_2O$): δ7.50 (1H,s), 7.00 (1H,s), 5.00 (1H,d), 4.61 (1H,m), 4.25 (1H,dd), 4.10 (1H,dd), 3.50 (2H,m), 3.35 (1H,dd), 3.25 (1H,dd), 2.45 (1H,m), 2.00 (1H,m), 1.75 (1H,m)

EXAMPLES 3-4

The procedures of Examples 1 and 2 were repeated, but replacing medium (B) with the following medium:

|  | g/l |
|---|---|
| Glycerol | 23.0 |
| L-proline | 11.5 |
| MOPS | 21.0 |

-continued

| | g/l |
|---|---|
| (3-(N-morpholino)propane sulphonic acid) | |
| EDTA | 0.25 |
| NaCl | 0.5 |
| MgSO$_4$.7H$_2$O | 0.49 |
| CaCl$_2$.2H$_2$O | 0.029 |
| K$_2$HPO$_4$ | 0.52 |
| Trace salts | 0.5 ml |
| pH | 6.5 |
| The trace salts contained: | |
| H$_2$SO$_4$ (1 M) | 10 ml |
| ZnSO$_4$.4H$_2$O | 8.6 g |
| MnSO$_4$.4H$_2$O | 2.23 g |
| H$_3$BO$_3$ | 0.62 g |
| CuSO$_4$.5H$_2$O | 1.25 g |
| Na$_2$MoO$_4$.2H$_2$O | 0.48 g |
| CoCl$_2$.6H$_2$O | 0.48 g |
| FeSO$_4$.7H$_2$O | 18.0 g |
| KI | 0.83 g |
| Distilled water to 1 liter. | |

The ingredients were dissolved in the distilled water in the order shown.

EXAMPLE 5

The crops and weeds listed in the table below were grown in sterilized loam in controlled environment rooms at 25° C. (non-temperate species) or 21° C. (temperate species). The plants were sprayed at an early growth stage. The compounds produced as in Example 2 and as listed below were each formulated in 25% methanol in distilled water, with 0.5% Tween 20 and 0.05% Pluronic L61 as wetters. The volume of the spray application was 2000 liters per hectare, giving an application rate of active ingredient of between 0.2 and 0.5 kg/ha. Treated plants were either returned to the controlled environment rooms or placed in glasshouses and assessed after 2 weeks, on a scale where 0 indicates no effect, 1 indicates slight damage, 2 indicates moderate damage, 3 indicates good control, and 4 indicates complete kill. In the following table, the compounds A1, A2, A3 and B1 are as identified hereinbefore.

The results obtained were as follows:

| | Compound | | | |
|---|---|---|---|---|
| | B1 | A1 | A2 | A3 |
| Rate (kg/ha) | 0.2 | 0.5 | 0.2 | 0.4 |
| Rice (*Oryzae sativa*) | 2 | — | — | — |
| Barley (*Hordeum vulgare*) | 1 | 3 | 2 | 1 |
| Cotton (*Gossypium hirsutum*) | 2 | — | — | — |
| Pale persicaria (*Polygonum lapathifolium*) | 2 | 4 | 4 | 2 |
| Corn Marigold (*Chrysanthemum segetum*) | 3 | 3 | 1 | 0 |
| Morningglory (*Pharbitis purpurea*) | 1 | 2 | 2 | 2 |
| Wild Oat (*Avena fatua*) | 0 | 2 | 1 | 2 |
| Couchgrass (*Agropyron repens*) | 0 | 2 | 0 | 1 |
| Blackgrass (*Alopecurus myosuroides*) | 1 | 2 | 2 | 2 |

EXAMPLE 6

| Characteristics of NCIMB 40131 | |
|---|---|
| Spore mass colour (ISP medium 4) | white |
| Substrate colour (ISP medium 4) | pale creamy orange |
| Spore chain shape (ISP medium 4) | short, flexous |
| Production of diffusive pigment (ISP medium 5) | — |
| Production of melanin (ISP medium 6) | — |
| Production of melanin (ISP medium 7) | — |
| Degradation of xanthine | — |
| Degradation of elastin | + |
| Degradation of hippurate | + |
| Degradation of pectin | +(weak) |
| Degradation of casein | + |
| Degradation of tyrosine | — |
| Growth on:- | |
| L-Rhamnose | + |
| Meso-Inositol | + |
| D-Melibiose | + |
| Glucose | + |
| Sucrose | + |
| Mannitol | + |
| Raffinose | — |
| Adonitol | + |
| Dextran | — |
| Xylitol | — |
| Utilisation of:- | |
| DL-α-Aminobutyric acid | + |
| L-Cysteine | — |
| L-Valine | + |
| L-Phenylalanine | + |
| L-Histidine | + |
| L-Hydroxyproline | — |
| Lipolysis | — |
| Lecithinase activity | — |
| Growth at:- | |
| 28° C. | + |
| 37° C. | poor |
| 45° C. | — |
| Growth with:- | |
| NaCl (7%, w/v) | — |
| NaN$_3$ (0.01%, w/v) | — |
| Phenol (0.1%, w/v) | — |
| Potassium tellurite (0.001%, w/v) | + |
| Thallous acetate (0.001%, w/v) | + |

The organism grows well on malt-yeast agar, oatmeal agar, and Bennett's agar, at 28° C. for 7-14 days.

The cell wall contains meso-diaminopimelic acid.

| Adonitol | — |
|---|---|
| Arabinose | + |
| Cellobiose | + |
| Galactose | + |
| Inositol | + |
| Lactose | + |
| Maltose | + |
| Mannitol | — |
| Melibiose | + |
| Raffinose | — |
| Rhamnose | + |
| Salicin | — |
| Sorbitol | — |
| Sucrose | + |
| Threhalose | + |
| Xylose | + |
| Fructose | + |
| Glycerol | + |
| Mannose | + |

We claim:

1. A herbicidal composition which comprises from 0.01 to 99% by weight of one or more 3,6,7,8-tetrahydro-imidazo [4,5-d]-[1,3]diazepin-8-ol derivatives of the formula:

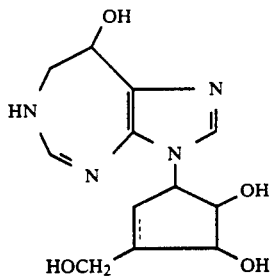

(I)

where the dotted line indicates that the bond between the two carbon atoms may be either a single or a double bond, in association with a suitable agricultural carrier and/or surface active agent.

2. 3-[2,3-Dihydroxy-4(hydroxymethyl)cyclopentyl]-3,6,7,8-tetrahydroimidazo [4,5-d][1,3]diazepin-8-ol.

3. 8R-3-[(1R,2R3R,4R)-2,3-Dihydroxy-4-(hydroxymethyl)-cyclopentyl]-3,6,7,8-tetrahydroimidazo[4,5-d][1,3]-diazepin-8-ol.

4. In a method of applying an effective amount of herbicide to a locus where herbicidal activity is desired, the improvement which comprises employing as the herbicide, a compound of formula I as defined in claim 1.

5. The method of claim 4 in which said compound is 3-[2,3-dihydroxy-4-(hydroxymethyl)cyclopentyl]-3,6,7,8-tetrahydroimidazo [4,5-d][1,3]diazepin-8-ol.

6. The method of claim 4 in which said compound in 8R-3-[(1R, 2S, 3R, 4R)-2,3-dihydroxy-4-(hydroxymethyl)-cyclopentyl]-3,6,7,8-tetrahydroimidazo[4,5-d][1,3]-diazepin-8-ol.

* * * * *